(12) United States Patent
Sato et al.

(10) Patent No.: US 7,781,623 B2
(45) Date of Patent: Aug. 24, 2010

(54) METHOD FOR PRODUCING CARDANOL (II)

(75) Inventors: Setsuo Sato, São José dos Campos (BR); Wanderson Bueno De Almeida, São José dos Campos (BR); Ramiro Carielo Bueno, Jacarei (BR); Alexssander Shigueru Araujo, São José dos Campos (BR)

(73) Assignee: Cognis IP Management GmbH, Duesseldorf (DE)

( * ) Notice: Subject to any disclaimer, the term of this patent is extended or adjusted under 35 U.S.C. 154(b) by 197 days.

(21) Appl. No.: 11/918,418

(22) PCT Filed: Apr. 5, 2006

(86) PCT No.: PCT/EP2006/003108

§ 371 (c)(1),
(2), (4) Date: Oct. 12, 2007

(87) PCT Pub. No.: WO2006/108546

PCT Pub. Date: Oct. 19, 2006

(65) Prior Publication Data

US 2009/0082598 A1    Mar. 26, 2009

(30) Foreign Application Priority Data

Apr. 14, 2005    (DE) .................. 10 2005 017 125

(51) Int. Cl.
C07C 29/80    (2006.01)
C07C 209/84    (2006.01)
C07C 209/90    (2006.01)

(52) U.S. Cl. .................. 568/810; 568/703; 568/780; 564/439

(58) Field of Classification Search .................. 568/780; 528/3; 435/6
See application file for complete search history.

(56) References Cited

U.S. PATENT DOCUMENTS 2,098,824 A * 11/1937 Harvey .................. 568/780
4,219,499 A * 8/1980 Hamprecht .................. 562/822
4,352,944 A * 10/1982 Tyman et al. .................. 568/766
6,229,054 B1  5/2001 Dai et al.
6,262,148 B1 * 7/2001 Cheng et al. .................. 523/458
6,846,389 B2 * 1/2005 Kaibel et al. .................. 203/1
7,244,772 B2 * 7/2007 Ittara et al. .................. 521/172

FOREIGN PATENT DOCUMENTS

GB    2 066 820 A    7/1981
GB    2 152 925 A    8/1985
GB    2 262 525 A    6/1993

OTHER PUBLICATIONS

Detwiler et al., 16 J. Am. Oil Chem. Soc., 2-5 (1939).*
Tyman et al., 80 J. Chem. Tech. Biotech., 1319-28 (2005).*
Joksic et al., Thermosetting Matrices Obtained from Cardanol Atti del XV Convegno Italiano di Scienza e Tecnologia dell Macromolecole, 24-27 (2001).*
Carioca et al., 2nd Mercosur Congress on Chemical Engineering and 4th Mercosur Congress on Process Systems Engineering, Poster HP-1-78 (2005).*
Database CAPLUS on STN, Acc. No. 1883:91106, JP 57140736 A (Aug. 31, 1982) (abstract).*
Farbe + Lack (1987), 93(7), p. 546-549 (CAPLUS abstract).*

* cited by examiner

Primary Examiner—Brian J Davis

(57) ABSTRACT

A process for the production of a color-stable composition containing cardanol, including (a) subjecting crude, cashew nutshell liquid to distillation to obtain a distillate; (b) reacting the distillate with acetic anhydride to obtain a reaction mixture; and (c) subjecting the reaction mixture to fractional distillation is provided. A method for the production of color-stable phenalkamines, including (a) subjecting crude, cashew nutshell liquid to distillation to obtain a distillate; (b) reacting the distillate with acetic anhydride to obtain a reaction mixture; (c) subjecting the reaction mixture to fractional distillation to obtain a cardanol-containing fractional distillate; and (d) reacting the fractional distillate with an aliphatic amine and formaldehyde to form a color-stable phenalkamine is also provided.

10 Claims, No Drawings

METHOD FOR PRODUCING CARDANOL (II)

CROSS-REFERENCE TO RELATED APPLICATIONS

This application is the national phase under 35 U.S.C. §371 of PCT International Application No. PCT/EP2006/003108 which has an International filing date of Apr. 5, 2006, which designated the United States of America and which claims priority on German Patent Application number DE 102005017125.7 filed Apr. 14, 2005, the entire contents of each of which are hereby incorporated herein by reference.

BACKGROUND OF THE INVENTION

1. Field of the Invention

This invention relates generally to an improved process for the production of cardanol from cashew nutshell liquid (CNSL). The process is distinguished by the fact that the cardanol thus obtainable contains fewer secondary products than the usual, commercially available cardanol.

2. Background Information

Phenalkamines are still a relatively young class of epoxy resin curing agents. They are products of the reaction (condensation products) of cardanol (I), which, chemically, is a $C_{15}$ alkylphenol and a major constituent of the oil obtainable from cashew nutshells (CNSL=cashew nutshell liquid), with aliphatic (primary or secondary) amines and formaldehyde.

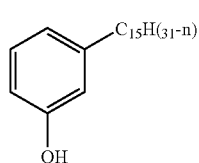

Cardanol (I)

Information on the class of phenalkamines can be found in the following publication: Zhishen Dai et al., "Phenalkamines: Multipurpose Epoxy Curing Agent"; Cardolite Corporation, Newark, N.J., USA; Reprint SPI-ERF Conference, September 1994.

It is known that crude CNSL predominantly contains a compound known as anacardic acid (II). The distillation of CNSL in the presence of acid gives a composition which mainly contains cardanol and, as a secondary product, cardol (III), cf. for example U.S. Pat. No. 6,262,148 and U.S. Pat. No. 6,229,054. This is consistent with applicants' own studies, according to which the distillation of crude CNSL gives a composition which mainly contains cardanol and, as a secondary product, cardol plus small quantities of 2-methyl cardol and anacardic acid.

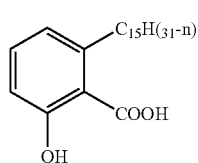

Anacardic acid (II)

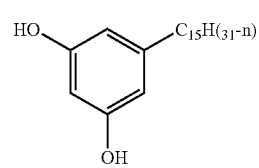

Cardol (III)

The cardanol/cardol mixture obtained in this way has three technical disadvantages:
- Its production by distillation from crude CNSL involves losses of value because part of the cardanol is lost through polymerization so that, ultimately, the yield of cardanol in the distillate is only 50-60%.
- The initially pale yellowish cardanol/cardol mixture changes during storage, rapidly turning brown in color. This unwanted change in color is attributed to the presence of cardol and other unknown components formed in the production of CNSL or in the distillation of CNSL at high temperatures.
- Products ensuing from the cardanol/cardol mixture also undergo unwanted changes in color during storage.

It has been proposed to improve the color stability of cardanol/cardol mixtures by reducing the cardol content by special measures. To this end, it has been proposed first to react the cardol present in the CNSL largely selectively with aldehydes, amines or bases and hydroxides of alkali and alkaline earth metals and then to distil off the unreacted cardanol. Particulars of these processes for the production of cardanol with improved color stability can be found in GB-A-2,152,925, GB-A-2,066,820 and U.S. Pat. No. 4,352,944.

SUMMARY OF THE INVENTION

Briefly described, according to an aspect of the invention, a process for the production of a color-stable composition containing cardanol includes the steps of: (a) subjecting crude, cashew nutshell liquid to distillation to obtain a distillate; (b) reacting the distillate obtained in step (a) with acetic anhydride to obtain a reaction mixture; and (c) subjecting the reaction mixture obtained in step (b) to fractional distillation.

According to another aspect of the invention, a method for the production of color-stable phenalkamines includes (a) subjecting crude, cashew nutshell liquid to distillation to obtain a distillate; (b) reacting the distillate obtained in step (a) with acetic anhydride to obtain a reaction mixture; (c) subjecting the reaction mixture obtained in step (b) to fractional distillation to obtain a cardanol-containing fractional distillate; and (d) reacting the fractional distillate with an aliphatic amine and formaldehyde to form a color-stable phenalkamine.

DETAILED DESCRIPTION OF THE INVENTION

The present invention provides a process for the production of color-stable cardanol. In addition, products derived from the cardanol produced by this process, particularly phenalkamines, are color-stable.

It has surprisingly been found that this can be achieved by the following procedure: (a) crude CNSL is subjected to rapid distillation, the temperature and/or residence time being kept to a minimum in order to minimize unwanted reactions, such as oxidation, (b) the distillate is subjected to a special chemical treatment and (c) to subsequent fractional distillation. In a preferred embodiment, the distillate may then be subjected to a further treatment with chemical adsorbents.

The key steps of the process according to the invention are as follows:
1. distillation, more particularly short-path distillation, of crude CNSL,
2. reaction of the distillate ("crude cardanol") with acetic anhydride,
3. fractional distillation of the reaction mixture of step 2.

If desired, the main fraction of step 3 may be aftertreated with small quantities of adsorbents and/or reducing agents. This is an optional measure.

If desired, even the crude CNSL may be pretreated with acetic anhydride (before step 1).

The present invention relates to a process for the production of a color-stable composition containing cardanol, in which
1. crude CNSL (cashew nut shell liquid) is subjected to distillation, more particularly short-path distillation,
2. the distillate obtained is reacted with acetic anhydride and
3. the reaction mixture is subjected to fractional distillation.

The product obtainable by the process according to the invention contains at least 98% cardanol isomers. Cardol and methylcardols are only present in very small quantities, preferably below 0.05%.

The CNSL used in the process according to the invention is of natural origin. It is obtained by extraction from the shells of cashew nuts (i.e., nuts of the tree *Anacardium occidentale*) and can vary in its composition. Typically, it contains 60-65% cardanol, 2-10% cardol, 10-15% oligomers/polymers and 0-2% 2-methylcardanol and anacardic acid.

The process according to the invention provides a color-stable composition containing cardanol. This composition is not only color-stable in storage, the phenalkamines produced from it are also. In addition, the composition is distinguished by the fact that it has better dermatological compatibility than known commercially available products, so that handling and transportation are safer.

In a preferred embodiment, the main fraction of step 3 of the process according to the invention is aftertreated with small quantities of adsorbents and/or reducing agents. A further increase in color stability is achieved by the use of adsorbents and/or reducing agents.

The following observations apply to the three above-mentioned compulsory steps of the process according to the invention:

Step 1 comprises substantially removing oligomers (with molecular weights of 1,000 to 3,000) from the crude CNSL. This is done by distillation, even simple short-path distillation leading to excellent results. During this distillation, ca. 15-20% by weight of the CNSL is generally removed in the form of the oligomers mentioned. Short-path distillation is the preferred distillation method. It is associated with rapid completion of the process, so that secondary processes, such as polymerization or oxidation, are suppressed as far as possible or minimized. The short-path distillation is preferably carried out at temperatures of 220 to 260° C. and pressures of 1 to 5 mmHg. A short-path distillation apparatus equipped with a pre-evaporator is preferably used. The main fraction—the actual distillate from step 1—is also referred to as crude cardanol.

In step 2, the distillate from step 1 is reacted with acetic anhydride. Unwanted chromophores are chemically bound in this way. The quantity of acetic anhydride used is preferably 1 to 5% by weight, based on the distillate from step 1. A quantity of about 2 to 3% by weight is particularly preferred. The reaction temperature is preferably adjusted to a value of 50 to 70° C. The reaction time is preferably between 30 and 90 minutes and, more particularly, around 1 hour. Acetic acid formed is preferably removed (stripped off) continuously from the system.

The mixture from step 3 is then subjected to fractional distillation. A fractionating column with more than 6 theoretical plates is preferably used, the distillation being carried out continuously. In one embodiment, a typical fractionating column with a head, rectifying section, feed plate, stripping section and bottom is used for the continuous fractional distillation. The cardanols are removed at the upper end (head) of the column, the cardols at the lower end (bottom). In order to avoid overheating, the distillation is preferably carried out low temperatures. Preferred conditions are: 180 to 210° C./0.5 to 1.5 mmHg at the head of the fractionating column and 230 to 260° C./1.5 to 3 mmHg at the lower end of the column. The product stream at the lower end of the column contains a fraction which is rich in cardols and contains only small amounts of cardanols and acetic acid esters.

Whereas steps 1 to 3 are essential to the process according to the invention, step 4 is optional. Any impurities still present are largely removed in step 4. Basically, there are no limitations as to the nature of the adsorbents or reducing agents used. Examples of suitable reducing agents are sodium hydrosulfite ($Na_2S_2O_4$), sodium metabisulfite ($Na_2S_2O_5$), sodium borohydride ($NaBH_4$), lithium aluminium hydride ($LiAlH_4$), tin chloride ($SnCl_2$) or magnesium silicate. Suitable adsorbents are, for example, magnesium silicate or chemically equivalent compounds. The quantity of adsorbents or reducing agents used may be kept to a minimum. Quantities of 0.1 to 5% by weight (based on the main fraction obtained in step 3) are preferably used, quantities of around 1% by weight being particularly preferred.

The present invention also relates to the use of cardanol-containing mixtures obtainable by the process according to the invention for the production of color-stable phenalkamines.

EXAMPLES

Example 1

Process According to the Invention

Step 1:
1250 g/h of CNSL (from Resibras) were fed continuously into a short-path distillation apparatus equipped with a pre-evaporator running at 240° C./1 mmHg and 170° C./5 mmHg, respectively. Conditions: first runnings in the pre-evaporator=63 g/h; main fraction=940 g/h.

Step 2:
5000 g of the distillate from the main fraction of step 1 ("crude cardanol") were reacted with 12.5 g acetic anhydride for 1 hour at 60° C.

Step 3:
The material from step 2 was fed continuously into a degasifier (170° C./5 mmHg) to remove the acetic acid formed in step 2. From the degasifier, the material was fed into a fractionating column that was operated continuously (top: 200° C./1 mm Hg; bottom: 250° C./3 mmHg; reflux ratio: 0.30). 80% of the material used was removed at the top of the column (cardanol-rich fraction), 20% at the bottom (cardol-rich fraction with small amounts of cardanol and acetic acid esters).

Step 4:

The head product of step 3 was then mixed with 7 g of magnesium silicate. The mixture was stirred for 30 mins. at 50° C. and then filtered using a Sparkler filter. A pure and color-stable cardanol was obtained in this way.

Example 2

Determination of Color Stability

The color (Gardner color values) of the product obtained in accordance with the invention was immediately measured. The product was then stored at 90° C. in an electrically heated oven and its color was determined after 1 day and after 2 days. A commercially available cardanol was also subjected to the same storage test and its color values were determined in the same way. The results are set out in Table 1. The row beginning with "Example 1" contains the Gardner color values of the product of Example 1 according to the invention. The row beginning with "Standard" contains the Gardner color values of a commercially available cardanol (cardanol from Resibras).

TABLE 1

|  | Immediately | 1 Day | 2 Days |
| --- | --- | --- | --- |
| Example 1 | 1.1 | 2.5 | 3.0 |
| Standard | 3 | 4.9 | 8 |

It can be seen that the product according to the invention is far superior to the commercially available standard.

In addition, it was found that phenalkamines produced from the product of Example 1, amines (especially diethylamine) and formaldehyde were also distinguished by color stability.

What is claimed is:

1. A process for the production of a color-stable composition containing cardanol, comprising the steps of:
    (a) subjecting crude, cashew nutshell liquid to distillation to obtain a distillate;
    (b) reacting the distillate obtained in step (a) with acetic anhydride to obtain a reaction mixture; and
    (c) subjecting the reaction mixture obtained in step (b) to fractional distillation to provide a cardanol-containing fractional distillate.

2. The process according to claim 1, wherein step (a) comprises short-path distillation.

3. The process according to claim 1, wherein about 1 to about 5% by weight of acetic anhydride, based on the weight of the distillate, is reacted.

4. The process according to claim 1, further comprising the step of continuously removing the acetic acid formed in step (b).

5. The process according to claim 1, further comprising the step of removing the acetic acid by feeding to a degasifier, prior to step (c).

6. The process according to claim 1, wherein step (c) further comprises conducting the fractional distillation in a fractionating column with more than 6 theoretical plates.

7. The process according to claim 6, wherein step (c) is conducted continuously.

8. The process according to claim 1, further comprising the step of treating the product obtained by the process with adsorbents and/or reducing agents.

9. The process according to claim 8, further comprising the step of filtration, after the step of treating.

10. A method for the production of color-stable phenalkamines, comprising:
    (a) subjecting crude, cashew nutshell liquid to distillation to obtain a distillate;
    (b) reacting the distillate obtained in step (a) with acetic anhydride to obtain a reaction mixture;
    (c) subjecting the reaction mixture obtained in step (b) to fractional distillation to obtain a cardanol-containing fractional distillate; and
    (d) reacting the fractional distillate with an aliphatic amine and formaldehyde to form a color-stable phenalkamine.

* * * * *